United States Patent [19]

Mott

[11] 4,349,029
[45] Sep. 14, 1982

[54] DRAINAGE BALLOON CATHETER SYSTEM

[76] Inventor: Patricia A. Mott, 103 N. Central, Armstrong, Mo. 65230

[21] Appl. No.: 160,134

[22] Filed: Jun. 16, 1980

[51] Int. Cl.³ .............................................. A61M 25/00
[52] U.S. Cl. .................................. 128/349 B; 128/295
[58] Field of Search ............... 128/242, 243, 246, 276, 128/294, 295, 344, 349 B, 349 BV, 350 R, 350 V, DIG. 24, 129

[56] References Cited

U.S. PATENT DOCUMENTS

| | | | |
|---|---|---|---|
| 602,777 | 4/1898 | Scroggs | 128/129 |
| 2,919,697 | 1/1960 | Kim | 128/349 |
| 3,392,722 | 7/1968 | Jorgensen | 128/1 |
| 3,394,705 | 7/1968 | Abramson | 128/349 |
| 3,397,699 | 8/1968 | Kohl | 128/243 |
| 3,438,375 | 4/1969 | Ericson | 128/349 B |
| 3,516,410 | 6/1970 | Hakim | 128/350 R |
| 3,583,401 | 6/1971 | Vaillancourt et al. | 128/350 R |
| 3,626,950 | 12/1971 | Schulte | 128/350 R |
| 3,726,283 | 4/1973 | Dye et al. | 128/349 BV |
| 3,736,939 | 6/1973 | Taylor | 128/349 B |
| 3,811,448 | 5/1974 | Morton | 128/349 B |
| 3,851,650 | 12/1974 | Darling | 128/350 R |
| 3,889,686 | 6/1975 | Duturbure | 128/349 B |
| 3,954,110 | 5/1976 | Hutchison | 128/349 B |
| 4,056,101 | 11/1977 | Geissler et al. | 128/DIG. 24 |
| 4,211,233 | 7/1980 | Lin | 128/349 B |
| 4,241,733 | 12/1980 | Langston | 128/295 |

OTHER PUBLICATIONS

Merck Index, Merck & Co. Inc., Rahway, N.J., 1976, Idophor 4903.

Primary Examiner—Richard J. Apley
Assistant Examiner—J. L. Kroter
Attorney, Agent, or Firm—Litman, Day and McMahon

[57] ABSTRACT

A catheterization apparatus is provided having a catheter, a drainage hose, and a collection vessel. The catheter is of the endwelling type having a retention balloon for expansion while the head of the catheter is in the bladder or other cavity being drained thereby. The balloon when expanded comprises a plurality of wings or loops which function in cooperation with at least one aperture which communicates the interior bore or lumen of the catheter with the bladder such that the bladder cannot collapse about and occlude the aperture. In this manner, substantially little or no residual urine remains in the bladder during catheterization thereof, thus reducing significantly growth of bacteria within the bladder which would tend to cause a urinary tract infection. The catheter, hose, and vessel normally form a sealed system which is preferably only broken every 24 hours. The vessel is sized so as to accept at least a 24 hour output of urine and is preferably nonreusable. In particular, the vessel has a constricted neck which allows urine to slowly flow thereinto over a period of time but which restricts quick and easy emptying of the vessel for reuse. A hanger is also provided for the vessel which allows the vessel to be easily secured to a bed or a wheelchair.

16 Claims, 10 Drawing Figures

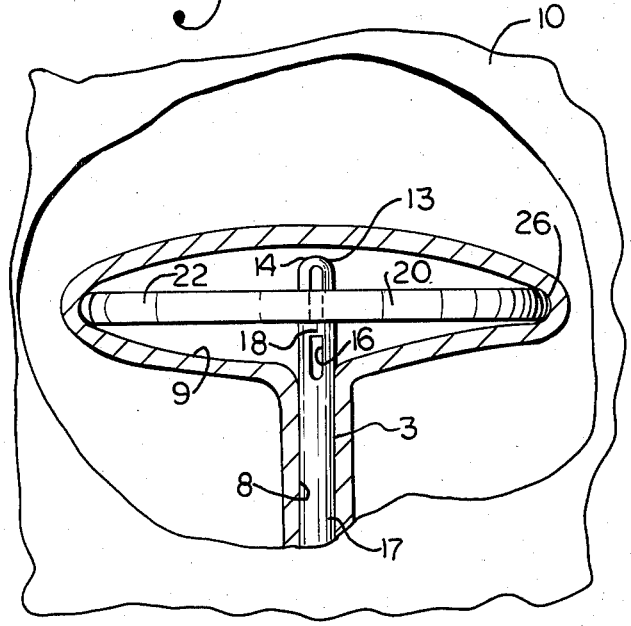
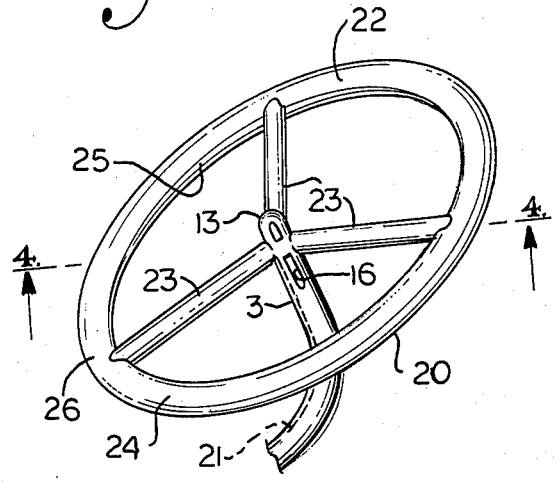
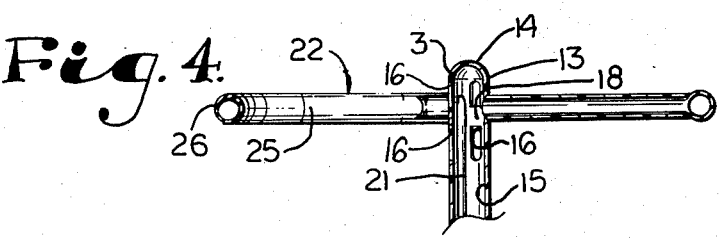
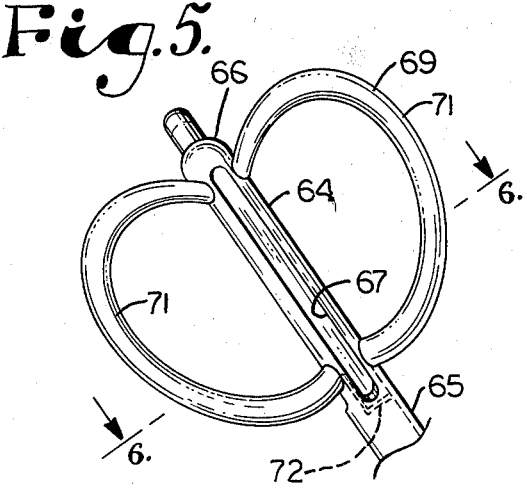
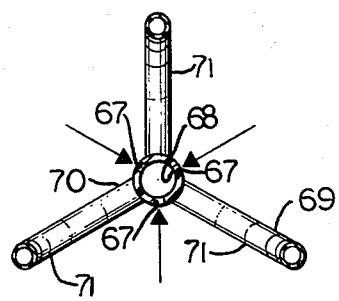

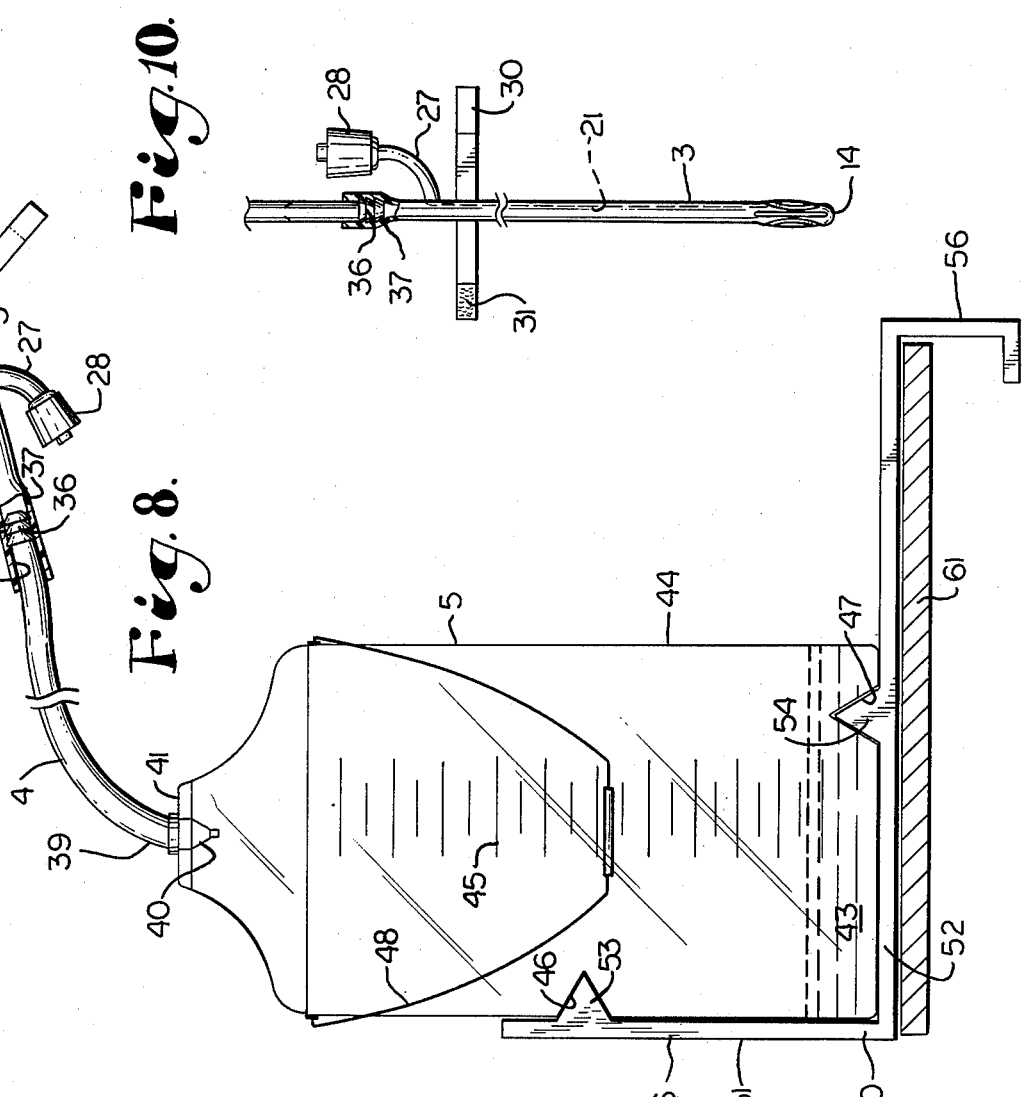
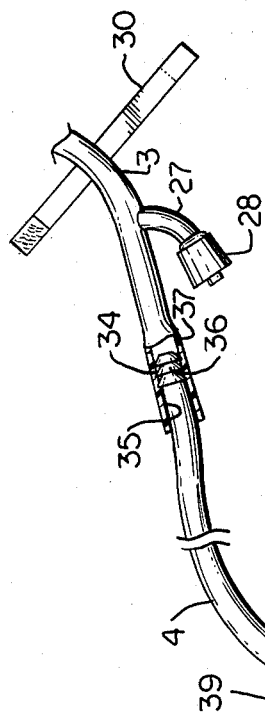
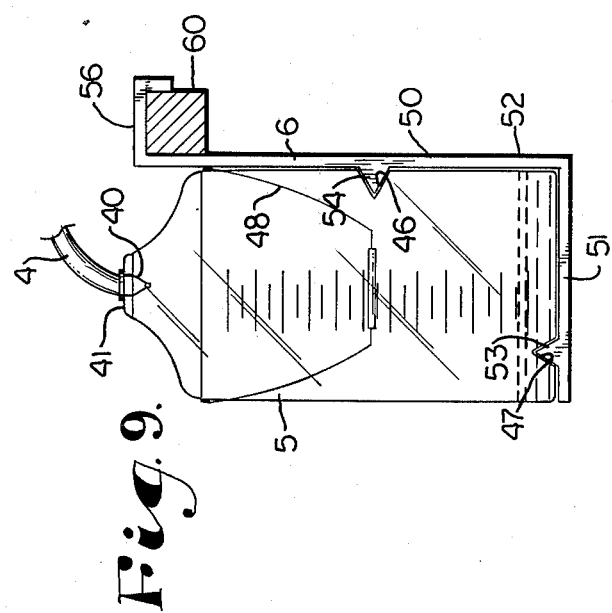
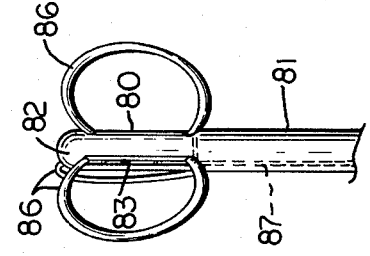

DRAINAGE BALLOON CATHETER SYSTEM

BACKGROUND OF THE INVENTION

The present invention relates to a catheter system and, in particular, to a retention type catheter utilizing a balloon-type structure to keep the catheter within a patient's bladder. The present invention is especially directed to a catheter system which reduces the possibility of nosocomial urinary tract infections caused by or enhanced by insertion and retention of an endwelling catheter.

A major cause of in-hospital or nosocomial infections, especially those of the urinary tract, have been linked to endwelling catheters. Although typically less than 2% of those patients catheterized by a non-endwelling or non-retention type catheter eventually develop a urinary tract infection, a substantial number of those patients requiring an endwelling catheter do eventually have such an infection. In fact, for those patients having an endwelling catheter for three days or more, the likelihood of urinary tract infection is as high as 98%. Although the exact scientific principals are not completely understood, applicant presently believes that bacteria enter the urinary tract both as a result of insertion of the catheter tube through an unsterile urethral opening and through migration of bacteria by Brownian movement from the periuethral or perianal orifices while the catheter is within the bladder. The urine in the bladder makes and excellent media for reproduction of bacteria which enters thereinto. Typically, these bacteria are in the nature of 60% *Escherichia colia* of which a concentration in the order of 10,000 per milliliter of urine is considered an infection of the urinary tract. In fact, a single bacteriium may typically reproduce in an eight hour period to as many as 130,000 to 33,552,000 bacteria. Applicant believes that substantial complete voiding of urine from the bladder such that substantially no residual urine remains therein will significantly reduce the number of bacteria reproducing therein and thus will significantly reduce the incidence of bacterial infection within the urinary tract. During normal function of the bladder when no catheter is present therein, the normal voiding of urine by the body tends to flush out bacteria such that few if any remain within the bladder to continue reproduction. Therefore, it would appear important that this normal complete voiding of the bladder continue after a catheter is inserted therein, especially when the catheter is potentially bringing additional bacteria to the bladder when it is inserted.

A number of previous catheter devices of the retention type have been developed for the purpose of completing draining urine from the bladder. In particular, a number of these devices have apertures both below and above the balloon or in the balloon itself so as to attempt to completely drain the bladder cavity. Although such drainage techniques have resulted in reduced infection rates, where such catheters have been used, there is still an extremely high incidence or urinary tract infection even with such devices. It is applicant's belief that the high incidence of infection is indirectly attributable to the pliability and elasticity of the bladder itself. In particular, the bladder tends to collapse when empty, which collapse tends to occlude or block the drainage apertures communicating between the bladder and the interior lumen of the catheter. In addition, drainage of the bladder may create a slight suction which would also tend to pull or hold the interior wall or mucosa lining the bladder against the apertures so as to keep a small residual amount of urine from entering thereinto. The present invention, therefore, is designed to positively restrain the walls and mucosa of the bladder from at least a portion of the apertures communicating between the interior of the catheter and the bladder, while insuring that such apertures are situated or positioned such that they will drain a maximum amount of residual urine from the bladder.

Another problem associated with conventional catheters is related to the insertion tip thereof. The tip in order to effect proper insertion must be somewhat resilient and hard in nature. It is believed that this tip tends to rub against and thus bruise or irritate the bladder lining opposite the opening of the uretha into the bladder. Such irritation over a period of time may tend to remove protecting mucosa from the lining of the bladder and also tend to enhance possibility of infection where the tip rubs. Therefore, it is desired to position the tip relative to the balloon such that the wider and, thus, less penetrating portions of the balloon tend to urge the bladder walls away from the tip.

Yet another problem associated with conventional catheter systems is that the urine collection container or bag, as is usually used, tends to promote bacterial growth within the system. In particular, the conventional systems normally have a rather small container which must be emptied on a regular basis, normally in the nature of every eight hours. Every time the seal of the system is broken so as to empty the container, bacteria are free to enter thereinto. In addition, many containers have lower spigots which are easy for bacteria to settle around and allow such bacteria to enter into the system when opened. Also, the urine tends to, as was previously mentioned, be an excellent growth media so as to promote bacteria growth within the container. It is also noted that there is typically no or insufficient support means for the container, especially when the patient must travel such as in a wheelchair or the like, so that the container is often pulled across the floor whereupon the container accumulates additional bacterial contamination therefrom. Finally, the conventional urine containers are often reusable or are manufactured in such a manner that they may be easily reused by an attendant pouring the urine therefrom. Such reuse tends to promote growth of residual bacteria remaining from the previous usage. Therefore, a containment vessel is provided herein which will preferably have only one small restricted opening for allowing the urine to enter thereinto, which opening is sufficiently small enough such that an attendant would not want to take the time to try to remove the urine therefrom, and, thus, the vessel is substantially nonreusable. Preferably, the vessel is designed to hold urine from at least a 24 hour period, such that the system need not be broken more than once in a 24 hour period, thereby reducing chance of contamination and reducing labor. The vessel also has included therein a sufficient amount of bacteriacide suitable for killing any bacteria which would normally enter into the vessel within a 24 hour period. Preferably, such a bacteriacide would be of such a nature so as not to interfere with tests which may be run on the urine or produce an allergic type of reaction within the patient. The bacteriacide may be eliminated should same interfere with tests for a particular patent. In addition, a hanger is provided which is adapted for holding the containment vessel securely on the rail of a hospital bed or on a foot plate of a wheelchair so as to maintain the containment vessel in an upright position in either case. Preferably, a sampling port is provided within the catheter system such that a sterile needle may be inserted into the system so as to remove urine therefrom without inserting bacteria.

OBJECTS OF THE INVENTION

Therefore, the objects of the present invention are: to provide an improved catheter system for retention type catheters such that incidence of urinary tract infection is substantially reduced; to provide such a catheter system including a retention balloon which cooperates with apertures communicating between the interior of the catheter and the bladder so as to positively restrain the walls of the bladder from occluding the apertures; to provide such a catheter system wherein the apertures are positioned so as to substantially drail all residual urine from the bladder; to provide such a catheter system having an insertion tip for the catheter which is positioned relative to the catheter balloon such that the walls of the bladder are not substantially irritated thereby; to provide such a catheter system which effectively maintains substantially no residual urine in the bladder; to provide such a catheter system including a collection vessel which is open to contamination not more than once every 24 hours; to provide such a collection vessel which is nonreusable; to provide such a collection vessel having substantially only one small opening thereinto which is substantially small enough to prevent an attendant from pouring collected urine therefrom so as to reuse the vessel; to provide such a catheter system wherein a bacteriacide is used within the collection vessel; so as to kill substantially all bacteria entering thereinto; to provide a method of catheterization utilizing the catheter system so as to reduce incidence of infection in a patient's urinary tract; and to provide such a catheter system which is economical to manufacture, efficient in use, and which is particularly well adapted for the proposed usage thereof.

Other objects and advantages of the present invention will become apparent from the following description taken in connection with the accompanying drawings wherein are set forth by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged partial view of catheter head within the bladder of a patient, as shown in FIG. 1.

FIG. 3 is a perspective view of a catheter head showing a balloon portion thereof expanded.

FIG. 4 is a cross-sectional view of a catheter head taken along line 4—4 of FIG. 3.

FIG. 5 is a perspective view of a first modified catheter head having retention balloons thereon expanded.

FIG. 6 is a cross-sectional view of the catheter head of FIG. 5 taken along line 6—6 of FIG. 5.

FIG. 7 is a perspective view of a third modified catheter head having retention balloons thereon in an expanded state.

FIG. 8 is a partial enlarged side elevational view of the catheter system showing a drainage hose, a collection vessel, and a hanger, positioned on a wheel chair or the like.

FIG. 9 is a partial enlarged side elevational view of the catheter system showing the collection vessel and hanger positioned on a bed or the like.

FIG. 10 is a partial enlarged top plan view of the catheter system showing the catheter with the retention balloon thereof in a nonexpanded position.

DETAILED DESCRIPTION OF THE PREFERRED EMBODIMENT

Figure 1:
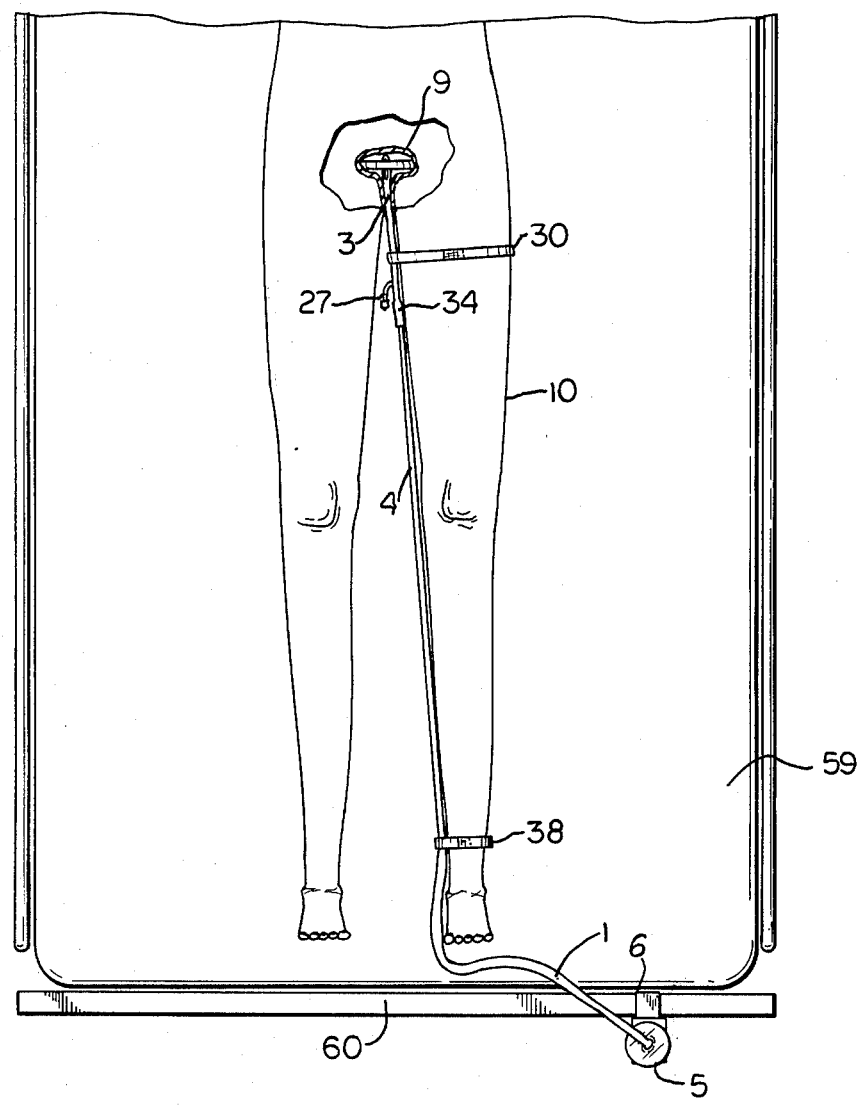
FIG. 1 is a top plan view of a catheter system according to the present invention shown with a catheter head inserted in a bladder of a patient.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed construction.

The reference numeral 1 generally designates a catheter system, according to the present invention, comprising a catheter 3, a drainage conduit, tube, or hose 4, a collection vessel 5, and a hanger 6 for the collection vessel 5.

The catheter 3 is of the endwelling or retention-type, which is suited for long term drainage of fluid from a body cavity. The illustrated catheter 3, as shown in FIGS. 1 and 2, is of the intraurethral type. The catheter 3 is inserted through the urethra 8 via the external body opening thereof into the bladder 9 of a patient 10 to be catheterized.

As used herein the term "upper", as used in conjunction with the catheter 3, refers in the direction of the top portion of the drawing as seen in FIG. 2 and the term "lower" refers to the opposite direction.

Positioned on the upper end of the catheter 3 is a head 13 adapted for being received within the bladder 9 to be catheterized. Positioned on the upper end of the catheter head 13 is an insertion tip 14 which must be substantially resilient and relatively hard enough to penetrate the urethra 8 during insertion of the catheter 3 therethrough. An interior bore or lumen 15, as seen in FIG. 4, extends throughout the length of the catheter 3. At least one opening, port, or aperture 16 flow communicates the upper end of the catheter lumen 15 with the interior of the bladder 9 when the catheter head 13 is within the bladder 9. The catheter 3 includes a urethra penetrating portion or shaft 17 which has the catheter head 13 and associated parts or apertures 16 at the upper end thereof. The catheter 3, illustrated in FIGS. 1 through 4, has a plurality of apertures 16 associated therewith, each of which apertures extend traversely or longitudinally along the shaft 17 both near the insertion tip 14 and near the opening of the urethra 8 into the bladder 9. Pairs of the apertures 16 are associated with one another such that each aperture 16 is traversely spaced from the other along the shaft 17 and separated from each other by a shaft support section 18.

The catheter head 13, shown in FIGS. 1 through 4, represents a first embodiment of the present invention wherein biasing means are utilized to positively urge the interior walls of the bladder 9 away from one or more of the apertures 16 so that the bladder walls or mucosa associated therewith will not block, obstruct, or occlude at least one of the apertures 16.

In particular, an expandable retention balloon 20 is attached to the catheter head 13 and is adapted to be expanded within the confines of the bladder 9 by insertion of a gas, such as air, or liquid fluid under pressure into the balloon 20 by means of a filling tube or channel 21 positioned within and generally extending along the catheter lumen 15. When expanded the balloon 20 of the present embodiment functions to retain the catheter 3 within the bladder 9 until the balloon 20 is deflated and also as the biasing means to positively urge the walls of the bladder 9 away from the apertures 16. The balloon 20 of the present embodiment includes when expanded, as seen in FIGS. 1 through 4, an outer donut shaped ring 22 surrounding and radially spaced from the catheter shaft 17 and especially spaced from the drainage apertures 16. The ring 22 is attached to the catheter shaft 17 by a plurality of spokes 23. The ring 22 and spokes 23 have a low profile with respect to the shaft 17 when not expanded, such as is illustrated in FIG. 10, so as to allow easy insertion of the catheter 3 into the urethra 8 and include suitable interior passageways (not shown) for communicating with the filling channel 21 such that the balloon ring 22 and spokes 23 may be selectively expanded and deflated by insertion of fluid thereinto. Preferably in this embodiment, at least one of the apertures 16 is positioned between each pair of adjacent spokes 23 and extends outward beyond each of the side of the spokes on the upper and lower side of the shaft 17.

In particular, each pair of adjacent spokes 23 and an associated portion of the ring 22 therebetween define a wing or loop 24 having an interior surface 25 which faces but is spaced from an associated drainage aperture 16 so that the associated aperture 16 opens into and flow communicates with the bladder 9 on opposite sides of the balloon 20 and an outer surface 26 which is opposite the inner surface 25 and which engages the walls of the bladder 9 when collapsed thereon.

A lower end of the catheter 3 includes a pressurization port 28 communicating with the filling channel 21 and having a suitable connector 27 adapted for use with a fluid pressurization unit (not shown) for expanding the balloon 20.

A sealing connector 34 secures the catheter 3 to the drainage hose 4 and allows flow of fluid therebetween. In particular, the illustrated connector 34 includes a resilient receiving end 35 in the lower end of the catheter 3 and a ribber upper end 36 of the hose 4 which sealably mates with the receiving end 35. A sample port 37 which forms a sterile seal near the lower end of the catheter 3 may be penetrated by a sterile syringe (not shown) or the like to withdraw a urine sample which may be accumulated at that location by occluding the hose 4 by pinching or the like for sufficient time to collect a sample. In the illustrated embodiment, a securing strap 30 suitable for wrapping about a leg of a patient 10 is secured to a lower end of the catheter 3 and includes a suitable quick connect fastener for securing opposite ends thereof together.

The hose 4 may be any structure suitable for allowing fluid flow therethrough. Preferably, the hose 4 is sealably connected at opposite ends thereof to the catheter 3 and collection vessel 5 and allows flow of fluid therethrough while preventing outside contamination, such as bacteria, into the fluid therein. A second strap 38 is attached to the hose 4 and adapted for securing about a lower portion of a leg of the patient 10. The lower end 39 of the hose 4 mates with the vessel 5. In particular, a constricted neck or restrictive orifice 40 or the like is positioned in the top of the vessel 41 through which orifice fluid passes as same discharges from the hose 4. The orifice 40 preferably is the only port into the collection vessel 5 and is sufficiently large to allow normal daily flow of urine from a patient to flow therethrough as same is discharged from the bladder 9 but is small enough to substantially restrict flow out of the vessel 5 such that the vessel 5 cannot be emptied in a short period of time, thereby dissuading an attendant from trying to empty the vessel 5 and substantially making the vessel 5 non-reusable.

The collection vessel 5 is preferably a somewhat rigid container suitable for holding fluid generally designated 43. The vessel 5 is shown with measuring indicia for allowing easy visual determination of the fluid 43 content thereof without need for a separate measuring device. The vessel 5 includes matching grooves 46 and 47 in the side and bottom thereof respectively which are equally spaced from a lower corner of the vessel 5. A handle 48 may also be attached to the vessel 5 to facilitate movement thereof.

The vessel fluid 43 preferably contains a predetermined amount of antiseptic solution inserted therein before use thereof. The antiseptic may be any suitable bacteriacide and is included in appropriate amounts to substantially kill all expected bacteria growth within urine entering the vessel 5 over at least a 24 hour period. Suitable antiseptics include hydrogen perioxide, vinegar, iodine, iodophor, alcohol, or combinations thereof. Preferably, the antiseptic chosen is non-allergenic to the patient and may be eliminated if same will interfere with hospital tests to be run on the urine in the fluid 43. Hydrogen perioxide is often well suited for this antiseptic purpose.

The hanger 6 has an L-shaped portion 50 having sides 51 and 52 to which are attached projections or teeth 53 and 54 respectively spaced and adapted for mating with the grooves 46 and 47 on the vessel 5. The hanger includes securing means such as a hook member 56 at one end of the L-shaped portion 50. The hanger 6 may be positioned such that the hook member 56 wraps about and holds the vessel 5 positioned thereon to a hospital bed 59 rail 60. When used on the bed 59, as seen in FIGS. 1 and 9, the teeth 53 and 54 engage the grooves 46 and 47 respectively of the vessel 5 and function as retention means for holding the vessel 5 in a selected location. Alternatively the hanger may be used in conjunction with a wheelchair or the like in which case the hook member 56 wraps about a foot plate 61 of the wheelchair, as seen in FIG. 8. When used such that the hook member 56 engages a horizontal surface, such as the plate 61, the teeth 53 and 54 mate with the grooves 46 and 47 respectively on the vessel 5. In this manner the single hanger 6 may be utilized to securely support the vessel 5 in an upright position on both a bed, wheelchair or the like.

The catheter system including the interconnected catheter 3, drainage hose 4 and collection vessel 5 is placed in use by insertion of the catheter 3 into the urethra 8 until the catheter head 13 is within the bladder 8 which is normally visually determined by noticing when urine starts to flow within the catheter 3. Balloon pressurizing fluid is inserted into the balloon 20 by means of the pressurization port 27 such that the balloon 20 expands in the bladder 9. The expanded balloon 20 positively urges the walls of the bladder 9 away from the catheter drainage aperture 16, as seen in FIG. 2. The insertion tip 14 preferably has a low profile relative to the balloon 20 such that the walls of the bladder 20 are also urged away from such a tip, as is also seen in FIG. 2. Urine flows from the bladder through the apertures 16, catheter lumen 15, and drainage hose 4 into the collection vessel 6 wherein same mixes with the fluid 43 therein including an antiseptic. Preferably, the system is broken only once every 24 hours to change collection vessels 5 so as to reduce chance of contamination and labor. The apertures 16 open into all parts of the bladder 3 so as to allow free flow into the catheter 3 of any urine originating in the bladder 9 and substantially eliminates any residual urine in the bladder 9. The hanger 6 allows the collection vessel 5 to be secured to a bed rail or wheelchair and is designed to be quickly adapted for moving from one to the other.

A second alternative catheter head 64 is illustrated in FIGS. 5 and 6. The head 64 has an associated catheter shaft or tube 65 which is attached to a drainage hose (not shown) as in the previous embodiment and an insertion tip 66. The head 64 includes three ports or drainage apertures 67 which flow communicate between an interior bore 68 of the tube 65 and the ambient surroundings thereof, as is shown by the arrows in FIG. 6. Each of the apertures 67 extend from near the tip 66 longitudinally along the tube 65 to that position on the tube 65 normally associated with being located near where the urethra 8 opens into the bladder 9 when the head 64 is inserted into the bladder 9. The balloon 69 has three individual loops 71 which are filled with fluid for expansion by means of a filling passageway 72 communicating with each loop 71 and running interior of and generally parallel to the bore 68. The loops 71 are generally arcuate and are attached to the tube 65 at a first end thereof near the tip 66 and at a second end thereof traversely spaced from the first end thereof along the tube 65. Preferably, the apertures 67 are positioned between adjacent loops 71 and extend somewhat above and below the attachment of each end of the loops 71 to the tube 65.

A third alternative catheter head 80 is illustrated in FIG. 7. The head 80 includes a cathete tube 81, insertion tip 82 at one end of the tube 81 and drainage apertures 83. The head 80 also has balloon loops 86 which are expanded by means of injecting fluid into an injection passageway 87 contained in the tube 81 and communicating with each loop 86. Each of the loops 86 is attached to the tube at a first end thereof near the tip 82 and at a second end thereof at a location spaced from the first end along the tube 81. Each loop 86 has associated therewith one of the apertures 83 extending from near the first end to near the second end of the associated loop 86. The loops 71 when deflated may be partly or totally positioned within the apertures 67.

Each of the second and third modified catheter heads 64 and 80 respectively are used in essentially the same manner as the first described head 13.

Although a certain number of balloon loops or rings have been disclosed in relation to the above embodiments, it is foreseen that any number of such loops can be utilized according to the invention as long as they do not interfere with free flow of urine into the catheter drainage ports or apertures such that substantially no residual urine remains within the bladder 9. Preferably, the rings or loops are symmetrically arranged on the catheter so as to evenly press against the walls of the bladder 9.

In addition, the present invention includes a method for reducing urinary tract infection during a retention-type catheterization by substantially eliminating residual urine in the bladder 9. The method comprises the steps of: inserting a catheter 3 having an aperture 16 for communicating between the interior bore 15 of the catheter 3 and the bladder 9 into the bladder 9 such that the aperture 16 is within the confines of the bladder 9; positively urging walls associated with the bladder 9 away from the aperture such that the walls do not block or occlude the aperture; the aperture 16 being characterized by opening into substantially all portions of the bladder 9; and allowing urine to freely drain from the bladder 9 through the aperture 16 into the catheter bore 15 and therethrough such that the urine is removed from the bladder 9 to a location external therefrom. Preferably, the walls of the bladder 9 are positively urged or biased by an expandable balloon 20 attached to the catheter 3 which balloon also urges the walls of the bladder 9 away from the insertion tip 14 associated with the catheter 3.

It is to be understood that while certain embodiments of the present invention have been described and shown herein, it is not to be limited to specific forms or arrangements of parts herein described and shown.

What is claimed and desired to secure by Letters Patent is:

1. In an intraurethral retention catheter having a longitudinal axis and being adapted for use in a bladder and having an expansion balloon for selectively maintaining the catheter after insertion within the bladder and at least one drainage aperture providing flow communication between an interior bore of the catheter and the bladder after insertion within the bladder; the improvement comprising:
   (a) expandable balloon biasing means including at least a first portion thereof radially extending and spaced outwardly and circumferentially from said catheter; and
   (b) said aperture being positioned on said catheter such that a plane normal to said catheter longitudinal axis and passing through said aperture also passes generally through said balloon biasing means; said balloon biasing means first portion being spaced radially outward from said aperture; whereby said aperture is adapted to freely communicate with urine within said bladder when said balloon biasing means is expanded and whereby said balloon biasing means is adapted to positively urge walls of the bladder away from the aperture when expanded within the bladder such that the walls do not occlude flow of urine from the bladder through the aperture.

2. The catheter according to claim 1 wherein:
   (a) said balloon biasing means is of an arcuate configuration and has inner and outer surfaces; a urine flow void exists between said aperture and said biasing means inner surface; said outer surface adapted for engaging the bladder walls and positively urging the walls away from said aperture; and said aperture opening into the bladder but in spaced relationship from said inner surface such that substantially all residual urine in the bladder can freely flow into the catheter by means of said aperture.

3. The catheter according to claim 2 wherein:

(a) a second and a third drainage aperture communicate between the catheter interior bore and the bladder above and below respectively the attachment of said balloon biasing means to a remainder of the catheter.

4. The catheter according to claim 3 wherein:
(a) said first, second, and third apertures are portions of a single continuous port.

5. The catheter according to claim 2 including:
(a) an insertion tip; said tip being oriented such that said balloon biasing means is adapted to urge the bladder walls away from said insertion tip when said catheter is inserted into the bladder so that said insertion tip does not continually rub against the bladder walls when inserted therein.

6. The catheter according to claim 2 wherein:
(a) said balloon biasing means comprises said expansion balloon and is attached to a lumen containing shaft of the catheter and includes a plurality of loops; and
(b) said aperture being associated with a first one of said loops and an additional respective aperture is associated with each remaining loop of said plurality of loops.

7. The catheter according to claim 6 wherein:
(a) each of said expansion balloon loops extend radially outward from the lumen containing shaft of said catheter in a symmetrical manner.

8. The catheter according to claim 7 wherein:
(a) said expansion balloon includes an outer donut shaped ring and a plurality of angularly spaced radially extending spokes attached at one end thereof to the shaft of the catheter and at the opposite end thereof to said ring for supporting said ring; adjacent spokes define said loops in conjunction with an associated portion of said ring therebetween.

9. The catheter according to claim 7 wherein:
(a) each of said loops are individually attached to said shaft at opposite first and second ends of the loop respectively; one end of each of said loops is attached at a first point near a distal end of said shaft and a second end of the respective loop is attached at a second point traversely spaced from said first point along said shaft; and
(b) each said associated aperture extends from near said first point of attachment to near said second point of attachment.

10. The catheter according to claim 1 in combination with:
(a) a vessel for collecting fluid from the cavity; and
(b) a drainage conduit flow communicating said drainage lumen with said vessel.

11. The catheter according to claim 10 wherein:
(a) said collection vessel has only one port thereinto; said port providing for flow of urine from said drainage conduit into said vessel; said vessel adapted for collecting urine from the bladder; said port having an opening sufficiently large enough to allow free flow of urine into said vessel over a normal time span for producing such urine within humans; and said vessel having a sufficiently small enough opening to substantially restrict flow of fluid from said vessel so as to dissuade an attendant from emptying urine from said vessel, whereby said vessel is made substantially not reusable.

12. The system according to claim 11 wherein:
(a) a bacteriacide is included in said vessel.

13. The system according to claim 12 wherein:
(a) said bacteriacide is selected from the group consisting of hydrogen peroxide, vinegar, iodophor, iodine, alcohol, and mixtures thereof.

14. The system according to claim 12 wherein:
(a) said bacteriacide is non-allergenic antiseptic compatible with normal hospital test run on urine.

15. The system according to claim 10 including:
(a) a hanger for said collection vessel; said hanger having hooking means thereon adapted for securing to both a bed frame and a wheelchair; said hanger also having retention means associated therewith for removably holding said vessel thereto both when said hanger is secured to the bed rail and when said hanger is secured to a wheel chair.

16. In a retention catheter with a longitudinal axis adapted for use in a bladder and having an expansion balloon for selectively maintaining the catheter after insertion within the bladder and at least one drainage aperture providing flow communication between the interior bore of the catheter and the bladder; the improvement comprising:
(a) expandable balloon biasing means spaced from said catheter in a plane normal to the catheter longitudinal axis and positioned circumferentially thereabout; said balloon biasing means for positively urging walls of the bladder away from the aperture such that the walls do not occlude flow of urine from the bladder through the aperture, said biasing means comprising said expansion balloon; said expansion balloon having an arcuate configuration with an inner and outer surface; said outer surface adapted for engaging the bladder walls; and said aperture opening into the bladder but in radially spaced relationship from said inner surface such that substantially all residual urine in the bladder can freely flow into the catheter by means of said aperture; wherein:
(b) said expansion balloon is attached to a lumen containing shaft of the catheter and has a plurality of loops;
(c) each of said loops has a drainage aperture associated therewith; and
(d) said expansion balloon includes an outer donut shaped ring and a plurality of angularly spaced radially extending spokes attached at one end thereof to the shaft of the catheter and at the opposite end thereof to said ring for supporting said ring; adjacent spokes define said loops in conjunction with an associated portion of said ring therebetween.

* * * * *